United States Patent [19]

Coulter

[11] 3,961,249
[45] June 1, 1976

[54] PARTICLE SIZE DISTRIBUTION ANALYZATION EMPLOYING TRAILING EDGE DIFFERENTIATION

[75] Inventor: Wallace H. Coulter, Miami Springs, Fla.

[73] Assignee: Coulter Electronics, Inc., Hiealeah, Fla.

[22] Filed: July 18, 1975

[21] Appl. No.: 597,081

Related U.S. Application Data

[63] Continuation of Ser. No. 404,035, Oct. 15, 1973, abandoned.

[52] U.S. Cl. .................................. 324/71 CP
[51] Int. Cl.² ................................ G01N 27/00
[58] Field of Search ............ 324/71 CP; 73/432 PS; 235/92 PC; 328/114, 115, 116

[56] References Cited
UNITED STATES PATENTS

| | | | |
|---|---|---|---|
| 2,656,508 | 10/1953 | Coulter | 324/71 CP |
| 3,345,502 | 10/1969 | Berg et al. | 324/71 CP X |
| 3,473,010 | 10/1969 | Bloomfield et al. | 324/71 CP |
| 3,529,239 | 9/1970 | Valley et al. | 324/71 CP |
| 3,560,847 | 2/1971 | Boyd et al. | 324/71 CP |
| 3,668,531 | 6/1972 | Hogg | 328/15 |

*Primary Examiner*—R. V. Rolinec
*Assistant Examiner*—Vincent J. Sunderdick
*Attorney, Agent, or Firm*—Silverman & Cass, Ltd.

[57] ABSTRACT

A particle analyzer for obtaining a narrow distribution of particles suspended in a liquid wherein electric pulses are produced by moving the liquid through a sensing zone. The analyzer includes elements for differentiating the pulses, short circuiting to ground pulse portions of one state and measuring the heights of pulse portions of another state as indications of particle sizes.

15 Claims, 4 Drawing Figures

U.S. Patent  June 1, 1976  3,961,249
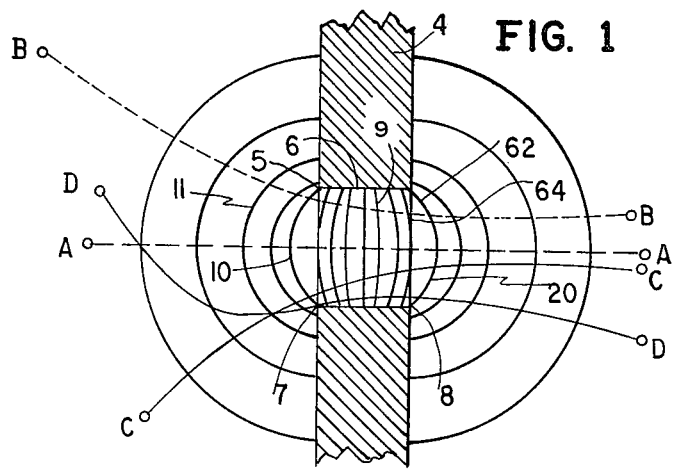
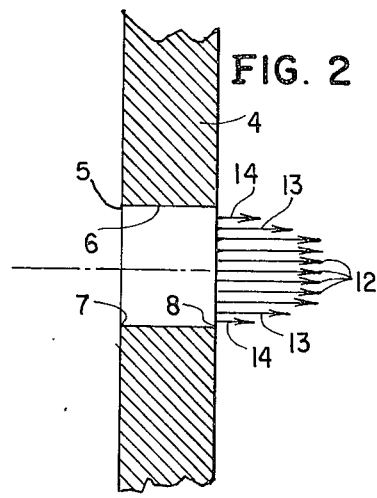
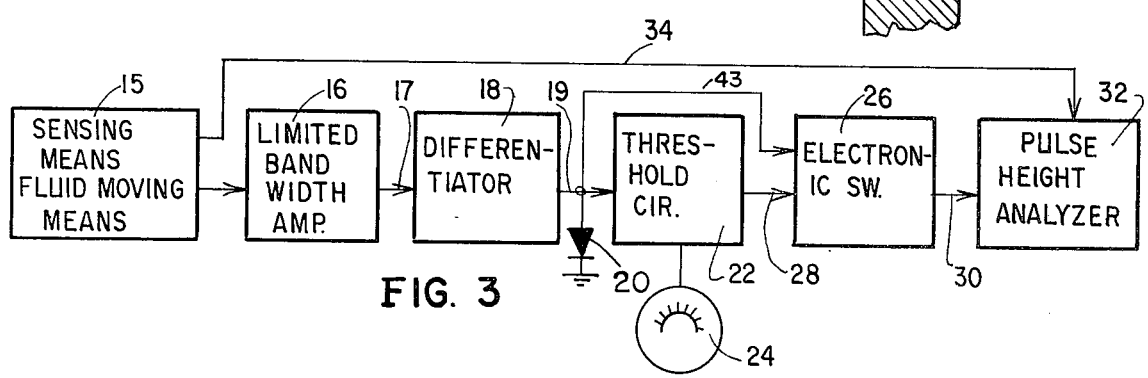
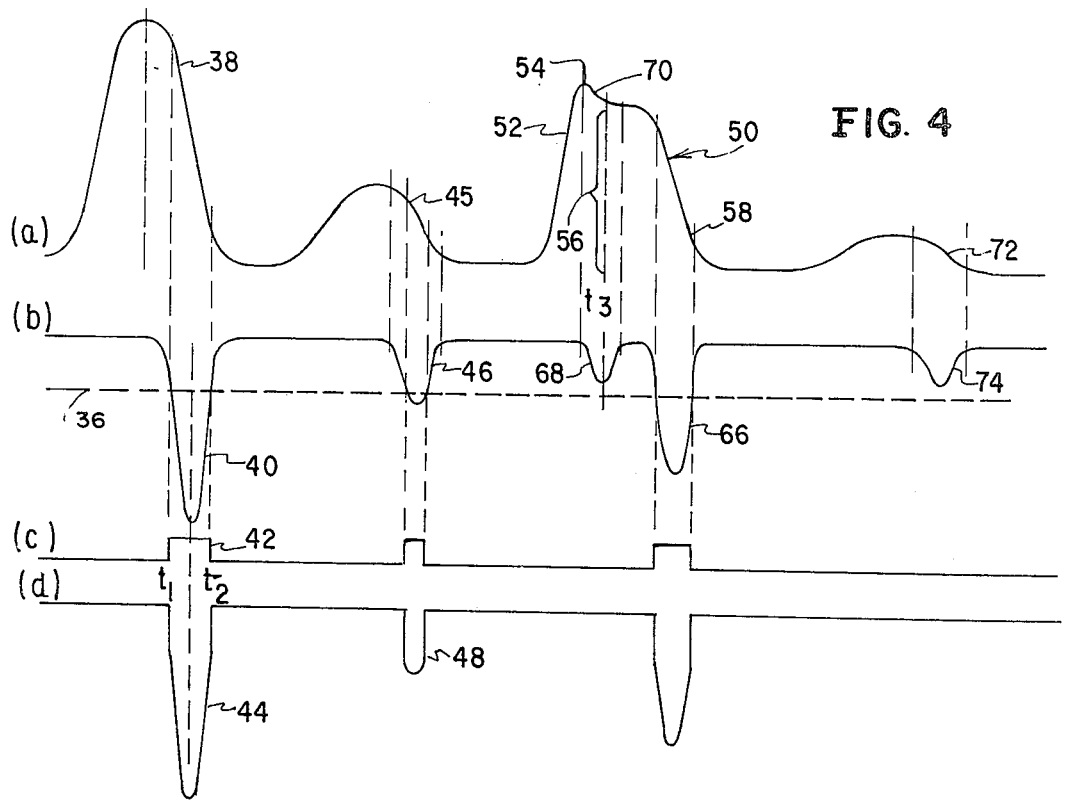

PARTICLE SIZE DISTRIBUTION ANALYZATION EMPLOYING TRAILING EDGE DIFFERENTIATION

This is a continuation of application Ser. No. 404,035, filed Oct. 15, 1973, and now abandoned.

BACKGROUND OF THE INVENTION

This invention relates to the art of particle size distribution analyzation and in particular to apparatus and method for making particle size distributions more narrow and free from artifacts.

To the extent that it might be necessary to understand fully the teachings of the invention herein, the following patents are incorporated by reference:
1. U.S. Pat. No. 2,656,508 to Wallace H. Coulter,
2. U.S. Pat. No. 3,668,531 to Walter R. Hogg.

U.S. Pat. No. 3,668,531 to W. R. Hogg for "Pulse Analyzing Apparatus", relating to art similar to that of this invention, uses apparatus which is responsive only to the amplitude formed at the center of a pulse.

The apparatus disclosed in U.S. Pat. No. 2,656,508 operates on a principle discovered by Wallace H. Coulter, known as the Coulter principle. In accordance with this principle, a sample quantity of a fluid suspension of the particles to be studied is caused to pass through a constricted path and the presence or absence of a particle gives rise to a detectable change in the electric characteristics of the path. That path is constructed so as to provide a region in which the electric field is substantially uniform or homogeneous and, at least in the case that the suspending fluid is a conductive liquid, the change is very nearly proportional to the volume of the particle which caused it.

In the usual commercial embodiment of the Coulter principle, the constricted path is achieved by a fine aperture in a wafer of insulating material which separates the sample suspension into two portions, each of which is connected to an electronic detector by means of a sensing electrode. These electrodes also supply the electrical current. The effective aperture bore usually will include fluid in regions slightly bulging out of the ends of the aperture convexly where the current density is relatively high, as will be seen hereinafter.

The passage of particles gives rise to electric signals which, when counted, give an accurate indication of the number of particles and, through the use of some form of amplitude discriminating means, the particles are classified according to their size by classifying the different amplitudes of pulses.

In order to obtain an electric signal, according to the U.S. Pat. No. 2,656,508, an electric current is established in the aperture. This is done by providing the aperture in a wall of an insulating material between two bodies of liquid, at least the upstream body having the sample suspension therein, immersing electrodes in each body of liquid, and connecting a suitable current source to the electrodes. The fluid is caused to flow from one fluid body through the aperture to the other body and, as it flows, the particles are carried through the aperture at a rapid rate. The impedance changes which are produced by the passage of each particle are detected by some form of electronic detector connected to the electrodes. In commercial versions of the "Coulter Counter" the electric signals produced are counted, displayed on a cathode ray oscilloscope, classified by various fixed and/or variable threshold circuits, recorded, and so on.

Generally, in the use of the apparatus for counting and sizing, as in most routine medical and biological work, the linearity of response of signals to particle sizes is not as important as in specific medical and biological research and in industrial studies. In the latter field, the dynamic range of particle size is quite great and often the entire spectrum of sizes must be studied.

Studies were made with a view towards ascertaining why there was a discrepancy in certain particle sizing investigations carried on in which the sizes of the particles as measured in accordance with the Coulter principle seemed greater than they should have been.

It was found that the center of a pulse is its more accurate part, since there could be false peaks at the beginning and end of pulses, caused by certain phenomena. For most purposes, the center of the signal pulse represents the detecting region having the most uniform field. In accordance with that finding, U.S. Pat. No. 3,668,531 suggests a solution to the problem of accurate particle analysis by means of apparatus which provides size information based upon a measurement of the amplitude of only the center of each pulse.

SUMMARY OF THE INVENTION

The present invention takes a different approach from that of the last mentioned patent to the problem of accurate particle analysis. The new approach is based on the concept of the use of the signal obtained by differentiating one of the edges of the particle pulse as an indication of the size of the particle.

As a matter of principle either one of the leading or trailing edges may be used for the purpose of obtaining a narrower distribution of pulses. In explaining the concept of the invention the focus will be on the trailing edge differentiation, it being understood that the inventive apparatus and method will operate equally well when using leading edge differentiation.

The basic observation underlying the invention is that particles which enter the aperture may enter at any point on the cross section of the aperture, but when they leave the aperture, they are most frequently caught up in the contracting jet-stream which is formed by the aperture. This means that the particles are shot out at the downstream end of the aperture with a speed which is very close to that of the electrolyte. At the upstream edge of the aperture, laminar flow has not been established yet. However, at the downstream side, particles which are radially positioned almost anywhere in the stream near the plane of the downstream edge of the aperture except for particles near the wall of the aperture will be going at almost uniform velocities. By differentiating the trailing edge of the particle pulses, a distribution of pulses is obtained which is proportional not only to the sizes of the particles, but to their velocities as well. This is not a major obstacle, because velocity is almost the same for all particles within the stream, and the resulting pulses are substantially proportional to particle volumes alone. Yet the distribution obtained is narrower than the distribution obtained merely by sensing the peaks of the particle pulses since false peaks may be involved.

The distribution is further narrowed by a threshold circuit cutting off pulses of values below a predetermined threshold value.

BRIEF DESCRIPTION OF THE DRAWINGS

FIG. 1 illustrates a cross section of a wafer and aperture, and isopotential surfaces which are established by the aperture current;

FIG. 2 is another cross section of the same wafer and aperture showing the approximate flow velocity distribution of electrolyte through the aperture measured in the plane on the downstream side of the aperture;

FIG. 3 is a block diagram of apparatus illustrating elements and circuitry based on the inventive concept; and FIG. 4 shows a series of waveforms, all to the same time scale, showing the signals at various connections within the apparatus.

BRIEF DESCRIPTION OF THE PREFERRED EMBODIMENT

Referring now to FIG. 1, which is substantially similar to the upper portion of FIG. 1 in the above noted U.S. Pat. No. 3,668,531 an illustration is given of the sectional profile of a wafer 4 in a "Coulter Counter" counting and sizing apparatus having an aperture 6 bored therein.

The structure is shown idealized, that is, with perfectly cylindrical bore and precisely sharp edges 7 and 8. When the aperture current is established in the apparatus, it flows through the aperture from one side to the other, as for example, from the left side to the right. The entire volume illustrated is filled with the sample liquid or electrolyte, but no symbols are used to illustrate this in order to keep the view simple. As the electric current passes through the liquid, the electric current density at the aperture is different than it is throughout other parts of the bodies of liquid through which the current passes. In the aperture itself, the electric current density will vary from location to location. Importantly, the current density at the lower corners 7 and 8 will be very much greater than anywhere else. Accordingly, at the upper corner 5, the current density will be equal to that of lower corner 7.

Also, isopotential lines are shown to be perpendicular at every point where they touch the outer surface of the wafer 4, being transverse of the aperture bore 6 and 9, slightly bulging out at the ends 10, and being quite arcuate at the outer surface of the bulge 11. The wafer is of insulating material. It will be appreciated that electric current density at any location is proportional to the number of equipotential surfaces in any given volume at that location. Although the current density in the aperture 6 generally is greater than it is outside of the aperture, the current density is a maximum at the corners 7 and 8, where the electric current turns the corner, so to speak, to enter the aperture 6 or exit therefrom and therefore, is greater than in the center of the aperture.

Three particles A, B and C are shown traversing the aperture from left to right along broken lines as shown and explained in detail in U.S. Pat. No. 3,668,531. An additional fourth particle D has a path similar but opposite to that of particle C as viewed from the axis of the aperture. The particle D starts out at the upper left side of the wafer 4, approaches the wafer and the axis thereof, traverses the aperture and continues on the right side thereof, but, as compared to the particle C, is further removed from the axis.

In FIG. 2 velocities in the electrolyte on the downstream side of the aperture 4 are illustrated by parallel vectors 12, 13 and 14 of varying magnitudes. The vectors 12 represent velocities at the axis of the stream and within a cylindrical formation therearound. The vectors 13 and 14 illustrate velocities outside said cyclindrical formation and closer to the wall of the aperture. The velocity vectors 13 and 14 are smaller than the velocity vectors 12 of the main portion of the electrolyte, the difference in magnitude being attributable to friction between the electrolyte stream and the wall of the aperture.

As a consequence of such velocity pattern, while particles entering the upstream side of the aperture will be subjected to more or less acceleration within the aperture depending upon whether they are closer or further away from the axis of the stream, over a large part of the cross-sectional area of the aperture they will be traveling with much the same velocity, as indicated by the vectors 12.

In the block diagram of FIG. 3, a sensing member 15 which may include the wafer with the aperture, an aperture current source, a manometer, stop and start contacts, and fluid moving means, is connected in series to an amplifier 16, the output thereof being coupled over lead 17 to a differentiator 18. The differentiator 18 may comprise a small capacitor and a resistor. The output side of the differentiator 18 connects via a line 19 to a diode 20 as well as a threshold circuit 22. The output side of the diode is connected to ground for a purpose to be described hereinafter. The threshold circuit 22 is controlled by an adjustment element 24 which may comprise a source of d.c. voltage and a potentiometer. An electronic switch 26 is connected via line 28 to the output of the threshold circuit 22. The output 30 of the electronic switch connects to a pulse height analyzer 32. There also is provided a path 34 from the sensing member 15 directly to the pulse height analyzer 32, on which path start and stop control signals may be transmitted. Such control signals, as usual in the prior art, may be actuated by manometer contacts.

Considering now FIG. 4, which illustrates waveforms of the signals and the operation thereof in various stages, it will be noted that the signal produced in the sensing member 15 by a particle passing therethrough is amplified in the amplifier 16 and is routed by lead 17 to the differentiator 18. It will be appreciated that the output of the differentiator at line 19 will be a positive signal for a positive going signal at lead 17, and a negative signal for a negative going signal at lead 17. Assuming that the positive going signals are caused by the leading edges of particle pulses, the present embodiment is not interested in those parts of the pulses, and the diode 20 placed between line 19 and ground, effectively short-circuits all positive signals.

The particle pulses are illustrated by four examples in graph (a) of FIG. 4. These are types of pulses which appear on lead 17 of FIG. 3. The differentiated and rectified pulses appearing on line 19 are shown in graph (b) of FIG. 4.

The source of d.c. voltage of the threshold circuit 22 establishes a d.c. level 36 of graph 4b.

A pulse 38 of FIG. 4a, when it subsides, produces a differentiated pulse 40 of FIG. 4b which, as indicated earlier, appears at line 19 of FIG. 3. This pulse 40 is used to actuate the threshold circuit 22 and produce at line 28 a pulse 42 of graph 4c. It will be appreciated that the leading and trailing edges of pulse 42 occurred at the times the pulse 40 crossed the d.c. voltage level 36. The pulse 40 also travels directly on line 43 to the electronic switch 26. The pulse 42 is used to turn on the electronic switch 26 which then applies on line 30 pulse 44, as shown in graph 4d. It is to be noted that pulse 44 is truncated at its skirts between the times $t_1$ and $t_2$.

Since the peak of pulse 40 passes through the electronic switch 26 unaltered, it may be considered a distinct measure of the size of the particle which produced the pulse 38, since pulse 40 is proportional to pulse 38.

The pulses are applied by line 30 to the pulse height analyzer 32 which produces a size distribution curve in any of conventional ways known in the prior art.

Looking now at another type of pulse, i.e. pulse 45 of graph 4a, it will be noted that such type of pulse is representative of a pulse produced by a smaller particle which goes along the axis of the scanning aperture 6. Upon differentiation, the pulse 46 of graph 4b is produced, resulting in the signal pulse 48 which appears on the line 30 of FIG. 3.

So far, it has been assumed that the particles which have been analyzed traversed the axis of the cylindrical aperture. However, it is known that frequently particles will proceed through the aperture on a path considerably non-axially and, as explained in U.S. Pat. No. 3,668,531, will produce irregularly shaped pulses. The pulse 50 in graph 4a is assumed to have been produced by a particle following path B of FIG. 1. It is noted that at the leading edge 52 of the pulse 50, there is an overshoot 54 due to the fact that the path B comes very close to the edge 5 of the aperture 6. As explained in the above noted U.S. Pat. No. 3,668,531, the instantaneous pulse value 56, which occurs at time $t_3$, is an accurate measure of the particle size.

At the trailing edge 58, however, the rate at which the pulse subsides would be slowed due to the fact that the liquid velocity is less, as illustrated in FIG. 2, but the rate change of voltage is greater because of the greater proximity of the isopotential surfaces 62 and 64. Therefore, the two effects tend to cancel, and the differentiated trailing edge 66 in graph 4b is still a reasonably accurate measure of the particle size.

Also, it is to be noted that the differentiated pulse 68 of graph 4b which was produced by the negative slope 70 of the pulse 50, was too small to exceed the threshold level 36 and, therefore, generates no output to the pulse height analyzer 52.

Another pulse 72 of graph 4a, although a regular pulse, produced by a particle traveling down the axis of the aperture, produced the trailing edge differential pulse 74 of graph 4b. However pulse 74 did not exceed the threshold level 26 and, therefore, was not included in the measurement.

Summing up, the operation and results obtained by apparatus and circuitry as shown in FIG. 3, are clearly indicated in the graphs a to d of FIG. 4. Specifically, the pulse forms in graph 4a represent the pulses originally produced in the sensing member 10. Graph 4b shows pulse forms after differentiation and rectification of the original pulses. The pulses in graph 4c are control pulses produced in the threshold circuit for controlling the electronic switch. Finally, graph 4d shows pulse forms which pass the electronic switch and arrive at the pulse height analyzer.

In comparing the pulses of graphs 4a and 4d, it is readily seen that the latter are not only fewer in number but also more plain and simple, and yet are capable of giving a clear and distinct picture of the sizes of particles which produced the original pulses. This simple result is accomplished by giving consideration only to the trailing slopes of the original pulses and processing them as described earlier.

It is believed that the foregoing adequately will enable those skilled in the art to appreciate and practice this invention, and if necessary, make modifications which will fall within the scope of the invention. As an example, the amplifier 16 may be used to amplify the particle produced pulses to reasonable values, but in certain situations may, be entirely omitted. Also, in the case of distribution analysis based on leading edge differentiation rather than trailing edge differentiation, the diode-ground arrangement, earlier described as short-circuiting the positive going pulse portions may be modified so as to short-circuit the negative going pulse portions. Furthermore, the aforementioned pulse height analyzer may be replaced by a device analyzing other parameters of pulses.

What it is sought to be protected by U.S. Letters Patent is:

1. In a method for particle distribution analyzation, each particle when passing through a sensing zone producing a pulse having an amplitude proportional to the size of the particle, said method comprising the steps of: differentiating at least one edge of each particle-produced pulse, short-circuiting to ground the other edge of each particle-produced pulse, passing the differentiated pulse to a limiting stage to produce signals for controlling the passage of a part of the differentiated pulse to pulse amplitude analyzing means, and employing the height of the resulting differentiated pulse part as a measure of the size of the original particle-produced pulse.

2. The method set forth in claim 1 in which the differentiated edge of the particle-produced pulse is the trailing edge thereof.

3. The method set forth in claim 1 comprising the step of amplifying the particle-produced pulses to desirable values prior to the differentiation thereof.

4. A method for particle distribution analyzation of particles suspended in a liquid, an aperture being arranged in an insulating wall separating the liquid into two bodies, each particle when passing through the aperture producing a pulse proportional to the size of the particle, said method comprising the steps of:
   a. differentiating at least one edge of each particle-produced pulse,
   b. short-circuiting to ground the other edge of each particle-produced pulse,
   c. passing the differentiated pulse to a limiting stage to produce signals for controlling the passage of a part of the differentiated pulse to pulse amplitude analyzing means, and
   d. employing the height of the resulting differentiated pulse part as a measure of the size of the original particle-produced pulse.

5. The method as set forth in claim 4 in which the differentiated edge of the particle-produced pulse is the trailing edge thereof.

6. Apparatus for particle distribution analyzation, each particle in passing through a sensing zone producing a pulse having an amplitude proportional to the size of the particle, said apparatus comprising:
   a. means for differentiating at least one edge of each particle-produced pulse,
   b. means for short-circuiting to ground the other edge of each particle-produced pulse, c. means for analyzing the amplitude of part of each differentiated pulse as an indication of particle size, whereby a narrow particle distribution is obtained, and d. a limiting stage coupled between said differentiating means and said amplitude analyzing means to produce signals for controlling the passage of a part of the differentiated pulse to the pulse analyzing means.

7. Apparatus as set forth in claim 6 in which the differentiated edge of the particle-produced pulse is the trailing edge thereof.

8. Apparatus as set forth in claim 6 including means for amplifying the particle-produced pulses prior to the differentiation thereof.

9. Apparatus as set forth in claim 6 connected to means for producing electric pulses comprising:
 a. an aperture in a wall of insulating material between two bodies of liquid,
 b. an electrode in each of said bodies,
 c. an aperture current source connected to the electrodes, and
 d. means for moving the liquid through the aperture.

10. Apparatus as set forth in claim 9 including an amplifier connected to the output of the pulse producing means for amplifying the particle-produced pulses to desirable values.

11. Apparatus as set forth in claim 6 in which the shortcircuiting means comprises a diode the input terminal thereof coupled to the output of the differentiating means and the output terminal of the diode connected to ground.

12. Apparatus as set forth in claim 6 in which the limiting stage includes a threshold circuit, a source of d.c. voltage and a potentiometer for adjusting the level of the threshold circuit.

13. Apparatus as set forth in claim 12 including an electronic switch having a first input terminal connected to the output of the threshold circuit, such that a pulse produced by the threshold circuit controls the electronic switch.

14. Apparatus as set forth in claim 13 in which a direct lead is provided between the output side of the differentiating means and a second input terminal of the electronic switch, for transmitting differentiated and rectified pulses to the electronic switch which is controlled by the threshold circuit.

15. Apparatus as set forth in claim 14, which includes particle pulse producing means having a manometer and contact means coupled thereto for generating stop and start signals, and in which the amplitude analyzing means is provided with a first and second input terminal, the first input terminal being connected to the output of the electronic switch, and the second input terminal being connected by a direct line to the pulse producing means, whereby start and stop signals may be transmitted from the manometer contact means to the amplitude analyzing means.

* * * * *